(12) United States Patent
Zaveri et al.

(10) Patent No.: US 9,062,042 B2
(45) Date of Patent: Jun. 23, 2015

(54) NICOTINIC ACETYLCHOLINE RECEPTOR MODULATORS

(75) Inventors: Nurulain T. Zaveri, Saratoga, CA (US); Faming Jiang, Mountain View, CA (US)

(73) Assignee: Astraea Therapeutics, LLC, Mountain View, CA (US)

( * ) Notice: Subject to any disclaimer, the term of this patent is extended or adjusted under 35 U.S.C. 154(b) by 379 days.

(21) Appl. No.: 13/004,801

(22) Filed: Jan. 11, 2011

(65) Prior Publication Data

US 2011/0172264 A1    Jul. 14, 2011

Related U.S. Application Data

(60) Provisional application No. 61/294,044, filed on Jan. 11, 2010.

(51) Int. Cl.
| | | |
|---|---|---|
| *A01N 43/22* | (2006.01) | |
| *A61K 31/44* | (2006.01) | |
| *C07D 221/02* | (2006.01) | |
| *A61K 31/439* | (2006.01) | |
| *C07D 519/00* | (2006.01) | |
| *C07D 451/14* | (2006.01) | |

(52) U.S. Cl.
CPC ............ *C07D 451/14* (2013.01); *A61K 31/439* (2013.01); *C07D 519/00* (2013.01)

(58) Field of Classification Search
USPC .......................................... 514/299; 546/112
See application file for complete search history.

(56) References Cited

U.S. PATENT DOCUMENTS

| | | |
|---|---|---|
| 4,835,162 A | 5/1989 | Abood |
| 4,920,127 A | 4/1990 | King et al. |
| 4,959,367 A | 9/1990 | King |
| 5,039,680 A | 8/1991 | Imperato et al. |
| 5,096,901 A | 3/1992 | Ward et al. |
| 5,198,447 A | 3/1993 | Tyres |
| 5,200,413 A | 4/1993 | King et al. |
| 5,223,511 A | 6/1993 | Turconi et al. |
| 5,248,684 A | 9/1993 | Suzuki et al. |
| 5,280,028 A | 1/1994 | Flynn et al. |
| 5,399,562 A | 3/1995 | Becher et al. |
| 5,446,050 A | 8/1995 | Rosen |
| 5,468,758 A | 11/1995 | Cereda et al. |
| 5,491,148 A | 2/1996 | Berger et al. |
| 5,637,596 A | 6/1997 | Varasi et al. |
| 6,077,846 A | 6/2000 | Qian et al. |
| 6,117,889 A | 9/2000 | Shen et al. |
| 6,392,045 B1 | 5/2002 | Peters et al. |
| 6,413,978 B1 | 7/2002 | Makovec et al. |
| 6,495,605 B2 | 12/2002 | McCullough et al. |
| 6,541,478 B1 | 4/2003 | O'Malloy et al. |
| 6,828,330 B2 | 12/2004 | Walker et al. |
| 6,849,620 B2 | 2/2005 | Walker et al. |
| 6,852,716 B2 | 2/2005 | Walker et al. |
| 6,858,613 B2 | 2/2005 | Rogers |
| 6,894,042 B2 | 5/2005 | Walker et al. |
| 6,897,219 B2 | 5/2005 | Peters et al. |
| 6,911,543 B2 | 6/2005 | Walker et al. |
| 6,919,359 B2 | 7/2005 | Piotrowski et al. |
| 6,951,849 B2 | 10/2005 | Kelly et al. |
| 6,951,868 B2 | 10/2005 | Walker et al. |
| 6,964,972 B2 | 11/2005 | Peters et al. |
| 2002/0042426 A1 | 4/2002 | Makovec et al. |
| 2003/0045540 A1 | 3/2003 | Wishka et al. |
| 2003/0105089 A1 | 6/2003 | Wishka et al. |
| 2004/0147522 A1 | 7/2004 | Wong et al. |
| 2004/0157878 A1 | 8/2004 | Rogers et al. |
| 2005/0176754 A1 | 8/2005 | Xie et al. |
| 2005/0222196 A1 | 10/2005 | Walker et al. |
| 2005/0228023 A1 | 10/2005 | Zaveria et al. |
| 2005/0234092 A1 | 10/2005 | Walker et al. |
| 2005/0250808 A1 | 11/2005 | Xie et al. |
| 2005/0282823 A1 | 12/2005 | Breining et al. |
| 2006/0079564 A1 | 4/2006 | Jansen et al. |
| 2007/0112019 A1* | 5/2007 | Napier et al. ................. 514/299 |
| 2009/0118326 A1 | 5/2009 | Jiang et al. |

(Continued)

FOREIGN PATENT DOCUMENTS

| | | |
|---|---|---|
| EP | 1 403255 | 3/2004 |
| JP | 4 208267 | 7/1992 |
| WO | WO 98/54182 | 12/1998 |
| WO | WO 00/32600 | 6/2000 |
| WO | WO 00/45846 | 8/2000 |
| WO | WO 02/20521 | 3/2002 |
| WO | WO 02/085357 | 10/2002 |
| WO | WO 2004/013137 | 2/2004 |
| WO | WO 2005/037832 | 4/2005 |
| WO | WO 2005/060947 | 7/2005 |
| WO | WO 2005/111038 | 11/2005 |
| WO | WO 2006/056863 | 6/2006 |
| WO | WO 2007/039563 | 4/2007 |
| WO | WO 2007/040280 | 12/2007 |

(Continued)

OTHER PUBLICATIONS

Coe et al., Varenicline: A α4β2 nicotine receptor partial agonist for smoking cessation. J. Med. Chem. 48: 3474-3477 (2005).

(Continued)

*Primary Examiner* — Kendra D Carter
(74) *Attorney, Agent, or Firm* — Sunil Singh; Syndicated Law, P.C.

(57) ABSTRACT

Provided herein are novel and selective high affinity α3β4 nicotinic acetylcholine receptor ligands and pharmaceutical compositions thereof. In other embodiments, provided herein are methods of treatment, prevention, or amelioration of a variety of medical disorders such as, for example, drug addiction or pain using the compounds and compositions disclosed herein. In still other embodiments, provided herein are methods for modulating a nicotinic acetylcholine receptor (nAChR). In still other embodiments, provided herein are methods of selectively antagonizing receptors such as, for example, the α3β4 nicotinic acetylcholine receptor using the compounds and compositions disclosed herein.

39 Claims, No Drawings

(56) References Cited

U.S. PATENT DOCUMENTS

2011/0172264 A1 7/2011 Jiang et al.
2013/0196964 A1 8/2013 Harter et al.

FOREIGN PATENT DOCUMENTS

| WO | WO 2008/019372 | 4/2008 |
| WO | WO 2009/044162 | 4/2009 |
| WO | PCT/US2007/023152 | 5/2009 |
| WO | WO 2009/058120 | 5/2009 |
| WO | WO 2009/067579 | 5/2009 |
| WO | WO 2010/113834 | 10/2010 |
| WO | WO 2011/085389 | 1/2011 |
| WO | PCT/US2011/020881 | 3/2011 |

OTHER PUBLICATIONS

Costa et al., Astructural model of agonist binding to the alpha3beta4 neuronal nicotinic receptor, British Journal of Pharmacology 140: 921-931 (2003).

Database Registry [Online] Chemical Abstracts Service, Columbus, Ohio, US: 9 XP002693363 Database accession No. 1026797-476 (Jun. 2008).

Database Registry [Online] Chemical Abstracts Service, Columbus, Ohio, US: 5, XP002693364, Database accession No. 1025834-81-4 (Jun. 2008).

Fernandez, et al., Synthesis and structural and conformational study of some amines derived from the norgranatane system. Journal of Molecular Structure, Elsevier, Amsterdam, NL, 246(3/04): 359-366 (Jan. 1, 1991).

PCT International Search Report for PCT US2007/023152, May 7, 2009.

PCT International Search Report for PCT US2011/020881, Mar. 29, 2011.

Supplementary European Search Report for EP 1173 2326, Mar. 7, 2013.

Lukas et al. International union of pharmacology. XX. Current Status of the Nomenclature for Nicotine Acetylcholine Receptors and their Subunits, Pharm, Rev., 51(2): 397-401 (1999).

Nielsen et al, Novel potent ligands for the central nicotinic acetylcholine receptor: synthesis, receptor binding, and 3D-QSAR analysis. Journal of Medicinal Chemistry, 43: 2217-2226 (2000).

Varma et al. Substituted N-Aminomethylisatins. Journal of Medicinal Chemistry,10: 510 (1967).

Yarnell Design of an antismoking pill. Chem & Eng. News, 83(23): 36-37 (2005).

Fernandez et al., Synthesis, and structural, conformational and pharmacological studies of new fentanyl derivatives of the norgranatane system. Journal of Chemical Society Perkins Transaction 2, 687 (1992).

\* cited by examiner

NICOTINIC ACETYLCHOLINE RECEPTOR MODULATORS

This application claims priority under 35 U.S.C. §119 (e) from U.S. Provisional Application Ser. No. 61/294,044, filed Jan. 11, 2010, which is hereby incorporated by reference in its entirety.

This invention was made with United States Government Support under Grant Number DA020811, awarded by the National Institute on Drug Abuse. Accordingly, the United States Government has certain rights to this invention.

FIELD

Provided herein are novel and selective high affinity α3β4 nicotinic acetylcholine receptor ligands and pharmaceutical compositions thereof. In other embodiments, provided herein are methods of treatment, prevention, or amelioration of a variety of medical disorders such as, for example, drug addiction or pain using the compounds and compositions disclosed herein. In still other embodiments, provided herein are methods for modulating a nicotinic acetylcholine receptor (nAChR). In still other embodiments, provided herein are methods of selectively antagonizing receptors such as, for example, the α3β4 nicotinic acetylcholine receptor using the compounds and compositions disclosed herein.

BACKGROUND

Nicotinic acetylcholine receptors are cholinergic receptors which form ligand gated ion channels and consist of a variety of subtypes. Nicotinic acetylcholine receptors regulate CNS and other physiological functions through mediation of the endogenous neurotransmitter acetylcholine. Accordingly, a wide variety of medical conditions (e.g., learning and eating disorders, neurodegenerative diseases, pain and chemical addiction) are associated with nicotinic acetylcholine receptors and may be treated or prevented with compounds that disrupt functioning of these receptors.

Thus, there is a continuing need for compounds that modulate nicotinic acetylcholine receptors and/or antagonize a particular receptor subtype to treat and/or prevent a variety of disorders such as for example, drug addiction, neurodegenerative disorders, pain, etc.

SUMMARY

The present invention satisfies this and other needs by providing compounds of Formula (I):

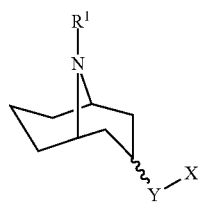

(I)

or salts, hydrates or solvates thereof wherein:

$R_1$ is hydrogen, alkyl, substituted alkyl, heteroalkyl, substituted heteroalkyl, arylalkyl, substituted arylalkyl, heteroarylalkyl, substituted heteroarylalkyl or —$CO_2R_2$;

$R_2$ is alkyl, substituted alkyl, heteroalkyl, substituted heteroalkyl, aryl, substituted aryl, arylalkyl, substituted arylalkyl, heteroaryl, substituted heteroaryl, heteroarylalkyl or substituted heteroarylalkyl;

Y is —$NR_3$;

$R_3$ is hydrogen, alkyl, substituted alkyl, heteroalkyl, substituted heteroalkyl, arylalkyl, substituted arylalkyl, heteroarylalkyl, substituted heteroarylalkyl, arylheteroalkyl or substituted arylheteroalkyl;

X is aryl, substituted aryl, heteroaryl or substituted heteroaryl;

provided that when $R_1$ is methyl and Y is —NH— that X is not phenyl and that when $R_1$ is H and Y is —NH— that X is not 3-chlorophenyl and that the compound of Formula (I) does not include N-(9-methyl-9-azabicyclo[3.3.1.]non-3-yl)-1H indazole-5-amine.

Methods of treating, preventing, or ameliorating medical disorders such as, for example, drug addiction drug addiction (e.g., cocaine addiction, opiate addiction (e.g., heroin, morphine, oxycontin tramdol, etc.), amphetamine (e.g., methamphetamine, dexedrine, MDMA, etc.), nicotine addiction, alcohol addiction, marijuana addiction, or combinations and modifications thereof), pain, neurodegenerative disorders, Parkinson's disease, Alzheimer's disease, and psychiatric disorders (e.g., schizophrenia) are also provided herein. In practicing the methods, effective amounts of the compounds or compositions containing therapeutically effective concentrations of the compounds are administered.

In some embodiments, methods for modulating a nicotinic acetylcholine receptor (nAChR) are provided herein. In other embodiments, methods of antagonizing receptors such as, for example, the α3β4 nicotinic acetylcholine receptor are also provided herein. In practicing the methods, effective amounts of the compounds of Formula (I) or compositions thereof are administered. In some embodiments, the compounds of Formula (I) are more than 10 times more selective for the α3β4 nicotinic acetylcholine receptor than the α4β2 acetylcholine nicotinic receptor.

DESCRIPTION

Definitions

Unless defined otherwise, all technical and scientific terms used herein have the same meaning as is commonly understood by one of ordinary skill in the art to which this invention belongs. In the event that there are a plurality of definitions for a term herein, those in this section prevail unless stated otherwise.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, refers to a radical of the formula —O—$R^{400}$, where $R^{400}$ is alkyl or substituted alkyl as defined herein.

"Acyl" by itself or as part of another substituent refers to a radical —C(O)$R^{401}$, where $R^{401}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Compounds" refers to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc.

Compounds may exist in unsolvated or unhydrated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups.

Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$, R$^{502}$, =N—N=, —N=N—, —N=N—NR$^{503}$R$^{404}$, —PR$^{505}$—, —P(O)$_2$—, —POR$^{506}$—, —O—P(O)$_2$—, —SO—, —SO$_2$—, —SnR$^{507}$R$^{508}$— and the like, where R$^{501}$, R$^{502}$, R$^{503}$, R$^{504}$, R$^{505}$, R$^{506}$, R$^{507}$ and R$^{508}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is (C$_1$-C$_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is (C$_1$-C$_3$) alkyl and the heteroaryl moiety is a 5-10 membered heteroaryl.

"Parent Aromatic Ring System" refers to an unsaturated cyclic or polycyclic ring system having a conjugated it electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). The application of a therapeutic for preventing or prevention of a disease of disorder is known as 'prophylaxis.' In some embodiments, the compounds provided herein provide superior prophylaxis because of lower long term side effects over long time periods.

"Protecting group" refers to a grouping of atoms that when attached to a reactive functional group in a molecule masks, reduces or prevents reactivity of the functional group during chemical synthesis. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^{31})$, —$P(O)(OR^b)(OR^b)$, —$C(O)R^b$, —$C(S)R^b$, —$C(NR^b)R^b$, —C(O)$O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Subject," "individual" or "patient" is used interchangeably herein and refers to a vertebrate, preferably a mammal Mammals include, but are not limited to, murines, rodents, simians, humans, farm animals, sport animals and pets.

"Treating" or "treatment" of any disease or disorder refers, in some embodiments, to ameliorating the disease or disorder (i.e., arresting or reducing the development of the disease or at least one of the clinical symptoms thereof). Treatment may also be considered to include preemptive or prophylactic administration to ameliorate, arrest or prevent the development of the disease or at least one of the clinical symptoms. In a further feature the treatment rendered has lower potential for longterm side effects over multiple years. In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, adsorption, distribution, metabolism and excretion etc., of the patient to be treated.

"Vehicle" refers to a diluent, excipient or carrier with which a compound is administered to a subject.

Compounds

Provided herein are compounds of Formula (I):

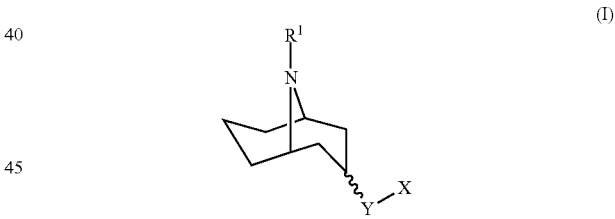

(I)

or salts, hydrates or solvates thereof wherein, $R_1$ is hydrogen, alkyl, substituted alkyl, heteroalkyl, substituted heteroalkyl, arylalkyl, substituted arylalkyl, heteroarylalkyl, substituted heteroarylalkyl or —$CO_2R_2$, $R_2$ is alkyl, substituted alkyl, heteroalkyl, substituted heteroalkyl, aryl, substituted aryl, arylalkyl, substituted arylalkyl, heteroaryl, substituted heteroaryl, heteroarylalkyl or substituted heteroarylalkyl, Y is —$NR_3$, $R_3$ is hydrogen, alkyl, substituted alkyl, heteroalkyl, substituted heteroalkyl, arylalkyl, substituted arylalkyl, heteroarylalkyl, substituted heteroarylalkyl, arylheteroalkyl or substituted arylheteroalkyl and X is aryl, substituted aryl, heteroaryl or substituted heteroaryl, provided that when $R_1$ is methyl and Y is —NH— that X is not phenyl, that when $R_1$ is H and Y is —NH— that X is not 3-chlorophenyl and that the compound of Formula (I) does not include N-(9-methyl-9-azabicyclo[3.3.1.]non-3-yl)-1H indazole-5-amine.

In some embodiments, $R_1$ is hydrogen, alkyl, substituted alkyl, arylalkyl, substituted arylalkyl or —$CO_2R_2$. In other embodiments, $R_1$ is hydrogen, alkyl or substituted alkyl. In still other embodiments, $R_1$ is hydrogen, methyl, ethyl,

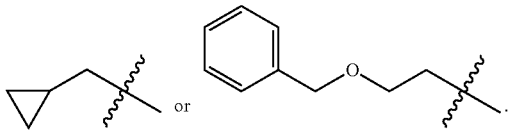 [SMILES: *CC1CC1 ; *CCOCc1ccccc1]

In still other embodiments, $R_1$ is arylalkyl or substituted arylalkyl. In still other embodiments, $R_1$ is

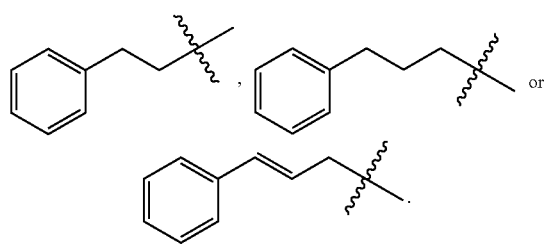

In still other embodiments, $R_1$ is phenyl or substituted phenyl. In still other embodiments, $R_1$

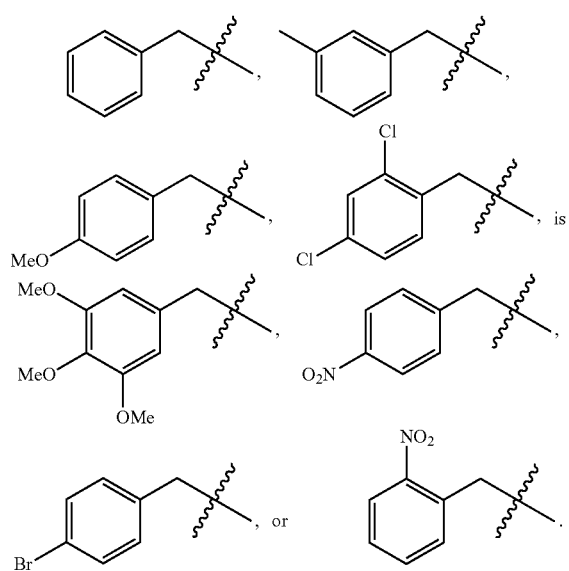

In some embodiments, $R_1$ is —$CO_2R_2$ and $R_2$ is disubstituted phenyl. In other embodiments, $R_2$ is

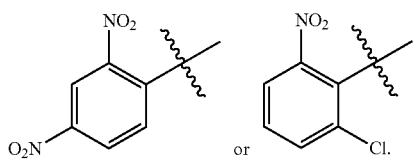

In some embodiments, X is phenyl or substituted phenyl. In other embodiments, X is o-substituted phenyl. In still other embodiments, X is

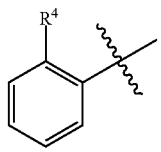

wherein $R_4$ is —Cl, —Br, —F, —I, —$CH_3$—$CF_3$, —$OCF_3$, —OH, —$CO_2$t-Bu, —$NO_2$, —$NH_2$, —$COCH_3$ or —CN.

In some embodiments, X is m-substituted phenyl. In other embodiments, X is substituted aryl. In still other embodiments, X is

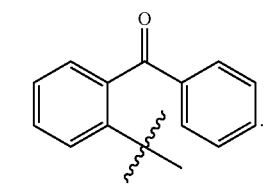 [SMILES: *c1ccccc1C(=O)c1ccccc1]

In some embodiments, X is heteroaryl or substituted heteroaryl. In still other embodiments, X is 2-pyridyl or 2-pyridyl substituted at the 5 position with —Br or —$NO_2$.

In some embodiments, $R_3$ is hydrogen, methyl, or alkyl. In other embodiments, Y is —NH— or —$NCH_3$—.

In some embodiments, $R_1$ is hydrogen, alkyl, substituted alkyl, arylalkyl, substituted arylalkyl or —$CO_2R_2$, X is aryl, heteroaryl, phenyl, substituted phenyl, o-substituted phenyl, m-substituted phenyl and Y is —NH— or —$NCH_3$—. In other embodiments, $R_1$ is hydrogen, alkyl or substituted alkyl, X is aryl, heteroaryl, phenyl, substituted phenyl, o-substituted phenyl, m-substituted phenyl and Y is —NH— or —$NCH_3$—. In still other embodiments, $R_1$ is arylalkyl or substituted arylalkyl, X is aryl, heteroaryl, phenyl, substituted phenyl, o-substituted phenyl, m-substituted phenyl and Y is —NH— or —$NCH_3$—. In still other embodiments, $R_1$ is —$CO_2R_2$, $R_2$ is disubstituted phenyl, X is aryl, heteroaryl, phenyl, substituted phenyl, o-substituted phenyl, m-substituted phenyl and Y is —NH— or —$NCH_3$—. In still other embodiments, $R_1$ is hydrogen, methyl, ethyl,

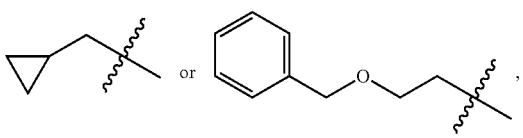 [SMILES: *CC1CC1 ; *CCOCc1ccccc1]

X is aryl, heteroaryl, phenyl, substituted phenyl, o-substituted phenyl, m-substituted phenyl and Y is —NH— or —$NCH_3$—. In still other embodiments, $R_1$ is

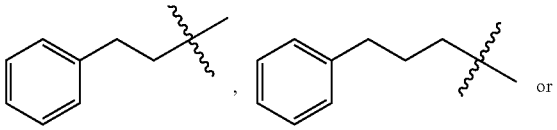

-continued

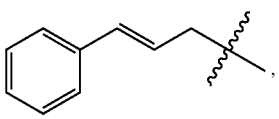

X is aryl, heteroaryl, phenyl, substituted phenyl, o-substituted phenyl, m-substituted phenyl and Y is —NH— or —NCH$_3$—. In still other embodiments, R$_1$ is

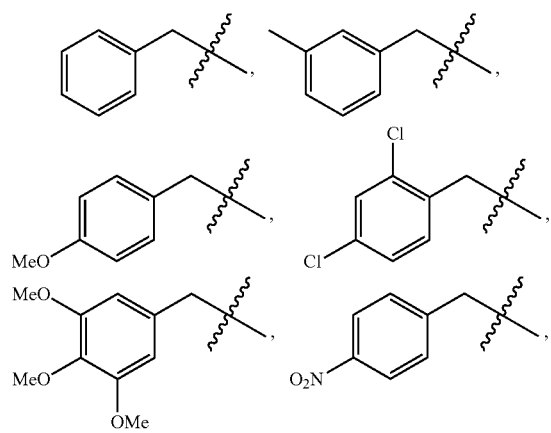

X is aryl, heteroaryl, phenyl, substituted phenyl, o-substituted phenyl, m-substituted phenyl and Y is —NH— or —NCH$_3$—. In still other embodiments, R$_1$ is —CO$_2$R$_2$, R$_2$ is

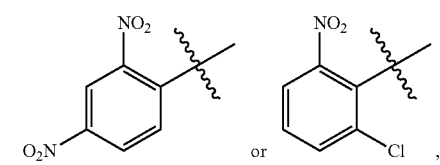 [SMILES: *c1ccc([N+](=O)[O-])cc1[N+](=O)[O-] ; *c1c(Cl)cccc1[N+](=O)[O-]]

X is aryl, heteroaryl, phenyl, substituted phenyl, o-substituted phenyl, m-substituted phenyl and Y is —NH— or —NCH$_3$—.

In some embodiments, R$_1$ is hydrogen, alkyl, substituted alkyl, arylalkyl, substituted arylalkyl or —CO$_2$R$_2$, X is

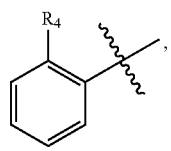

wherein R$_4$ is —Cl, —Br, —F, —I, —CH$_3$—CF$_3$, —OCF$_3$, —OH, —CO$_2$t-Bu, —NO$_2$, —NH$_2$, —COCH$_3$ or —CN and Y is —NH— or —NCH$_3$—. In other embodiments, R$_1$ is hydrogen, alkyl or substituted alkyl, X is

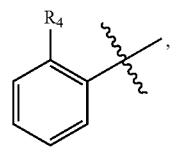

wherein R$_4$ is —Cl, —Br, —F, —I, —CH$_3$—CF$_3$, —OCF$_3$, —OH, —CO$_2$t-Bu, —NO$_2$, —NH$_2$, —COCH$_3$ or —CN and Y is —NH— or —NCH$_3$—. In still other embodiments, R$_1$ is arylalkyl or substituted arylalkyl, X is

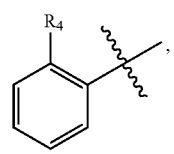

wherein R$_4$ is —Cl, —Br, —F, —I, —CH$_3$—CF$_3$, —OCF$_3$, —OH, —CO$_2$t-Bu, —NO$_2$, —NH$_2$, —COCH$_3$ or —CN and Y is —NH— or —NCH$_3$—. R$_1$ is —CO$_2$R$_2$, R$_2$ is disubstituted phenyl, X is

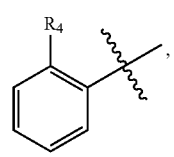

wherein R$_4$ is —Cl, —Br, —F, —I, —CH$_3$—CF$_3$, —OCF$_3$, —OH, —CO$_2$t-Bu, —NO$_2$, —NH$_2$, —COCH$_3$ or —CN and Y is —NH— or —NCH$_3$—. In still other embodiments, R$_1$ is hydrogen, methyl, ethyl,

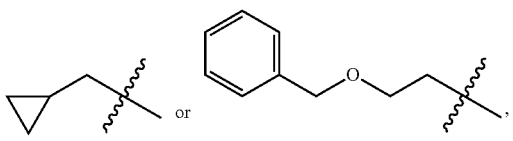

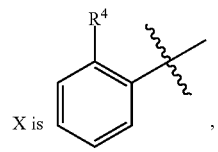

wherein R$_4$ is —Cl, —Br, —F, —I, —CH$_3$—CF$_3$, —OCF$_3$, —OH, —CO$_2$t-Bu, —NO$_2$, —NH$_2$, —COCH$_3$ or —CN and Y is —NH— or —NCH$_3$—. In still other embodiments, R$_1$ is

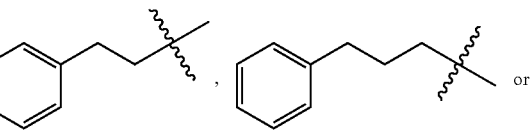

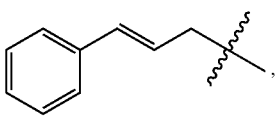

X is

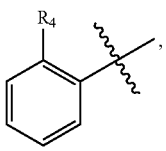

wherein $R_4$ is —Cl, —Br, —F, —I, —CH$_3$—CF$_3$, —OCF$_3$, —OH, —CO$_2$t-Bu, —NO$_2$, —NH$_2$, —COCH$_3$ or —CN and Y is —NH— or —NCH$_3$—. In still other embodiments, $R_1$ is

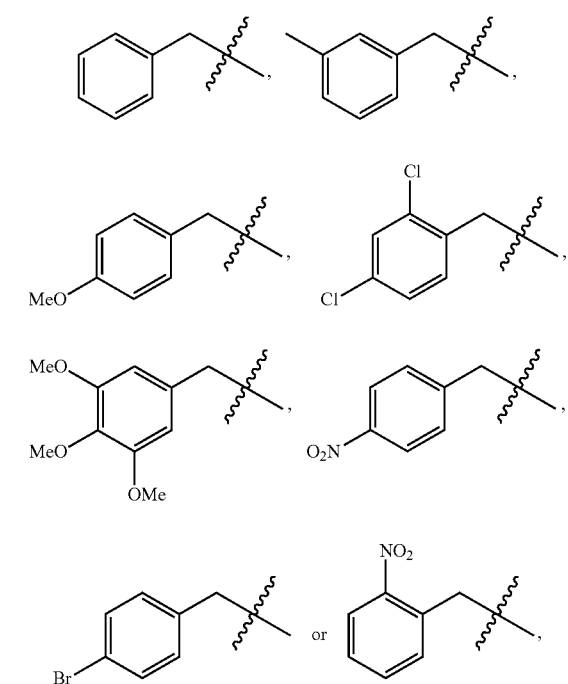

X is wherein $R_4$ is —Cl, —Br, —F, —I, —CH$_3$—CF$_3$, —OCF$_3$, —OH, —CO$_2$t-Bu, —NO$_2$, —NH$_2$, —COCH$_3$ or —CN and Y is —NH— or —NCH$_3$—. In still other embodiments, $R_1$ is —CO$_2$R$_2$, R$_2$ is

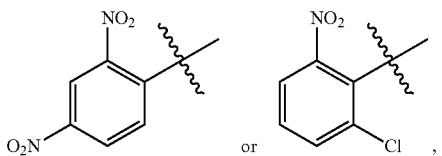

X is

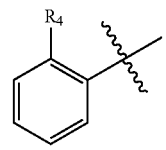

wherein $R_4$ is —Cl, —Br, —F, —I, —CH$_3$—CF$_3$, —OCF$_3$, —OH, —CO$_2$t-Bu, —NO$_2$, —NH$_2$, —COCH$_3$ or —CN and Y is —NH— or —NCH$_3$—.

In some embodiments, $R_1$ is methyl, Y is —NH and X is

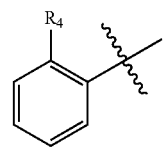

wherein $R_4$ is —Cl, —Br, —F, —I, —CH$_3$—CF$_3$, —OCF$_3$, —OH, —CO$_2$t-Bu, —NO$_2$, —NH$_2$, —COCH$_3$ or —CN. In other embodiments, $R_1$ is methyl, Y is —NH— and X is

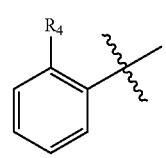

wherein $R_4$ is —Cl, —Br, —F, —I, —CF$_3$, —OCF$_3$, —NO$_2$ or —CN. In still other embodiments, $R_1$ is methyl, Y is —NH— and X is phenyl substituted at the meta position with bromo or chloro. In still other embodiments, $R_1$ is methyl, Y is —NCH$_3$— and X is

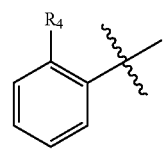

wherein $R_4$ is —Br. In still other embodiments, $R_1$ is hydrogen, Y is —NH— and X is

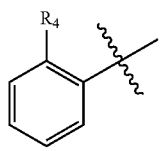

wherein $R_4$ is —$NO_2$.

In some embodiments, $R_1$ is methyl, Y is —NH— and X is 2-pyridyl or 2-pyridyl substituted at the 3 position with —Br or —$NO_2$. In other embodiments, $R_1$ is ethyl,

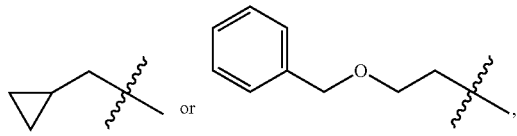 [SMILES: *CC1CC1 ; *CCOCc1ccccc1]

Y is —NH— and X is

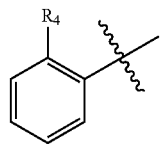

wherein $R_4$ is —Br. In still other embodiments, $R_1$ is methyl, X is 2-bromophenyl, Y is —$NR_3$—, and $R_3$ is —$CH_2CH_2OZ$, wherein Z is substituted phenyl. In some embodiments, Z is p-bromophenyl, m-methoxyphenyl or m-nitrophenyl.

The compounds of Formula (I) include the compounds depicted in Table 1 below:

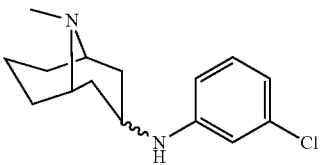 [SMILES: CN1C2CCCC1CC(Nc1cccc(Cl)c1)C2]
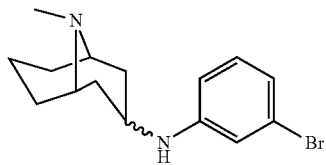 [SMILES: CN1C2CCCC1CC(Nc1cccc(Br)c1)C2]
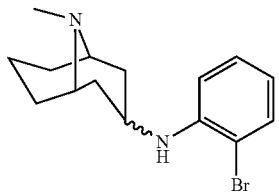 [SMILES: CN1C2CCCC1CC(Nc1ccccc1Br)C2]
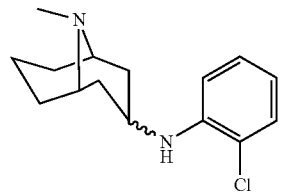 [SMILES: CN1C2CCCC1CC(Nc1ccccc1Cl)C2]
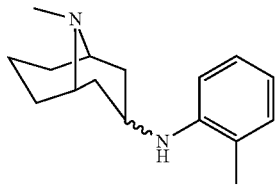 [SMILES: Cc1ccccc1NC1CC2CCCC(C1)N2C]
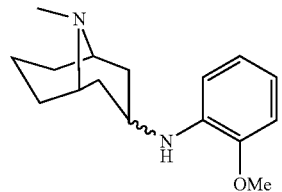 [SMILES: COc1ccccc1NC1CC2CCCC(C1)N2C]
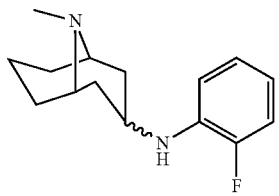 [SMILES: CN1C2CCCC1CC(Nc1ccccc1F)C2]
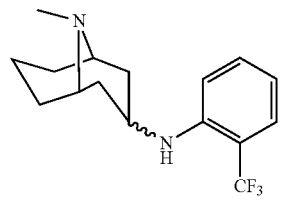
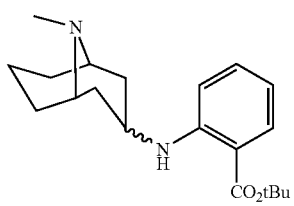 [SMILES: CN1C2CCCC1CC(Nc1ccccc1C(=O)OC(C)(C)C)C2]
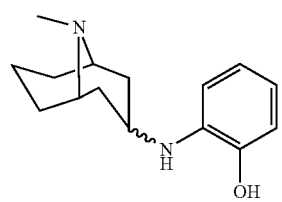 [SMILES: CN1C2CCCC1CC(Nc1ccccc1O)C2]

-continued
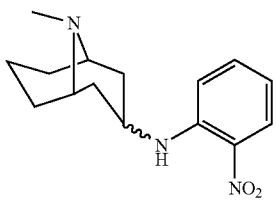 [SMILES: CN1C2CCCC1CC(Nc1ccccc1[N+](=O)[O-])C2]
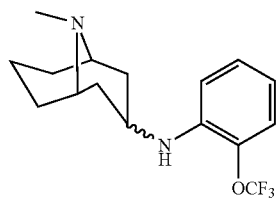 [SMILES: CN1C2CCCC1CC(Nc1ccccc1OC(F)(F)F)C2]
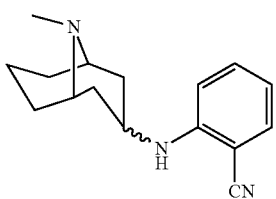 [SMILES: CN1C2CCCC1CC(Nc1ccccc1C#N)C2]
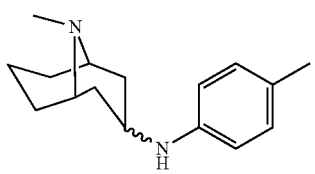 [SMILES: Cc1ccc(NC2CC3CCCC(C2)N3C)cc1]
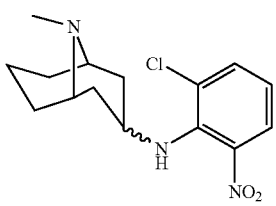 [SMILES: CN1C2CCCC1CC(Nc1c(Cl)cccc1[N+](=O)[O-])C2]
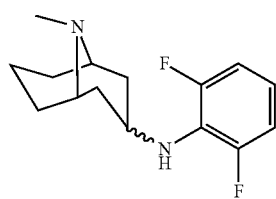 [SMILES: CN1C2CCCC1CC(Nc1c(F)cccc1F)C2]
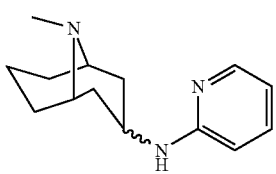 [SMILES: CN1C2CCCC1CC(Nc1ccccn1)C2]
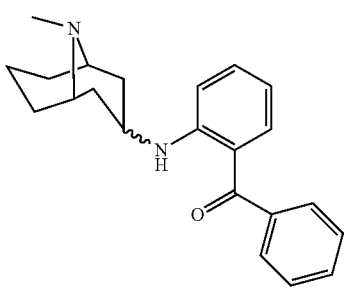 [SMILES: CN1C2CCCC1CC(Nc1ccccc1C(=O)c1ccccc1)C2]
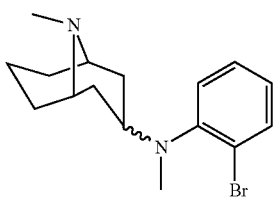 [SMILES: CN(c1ccccc1Br)C1CC2CCCC(C1)N2C]
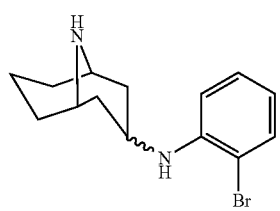 [SMILES: Brc1ccccc1NC1CC2CCCC(C1)N2]
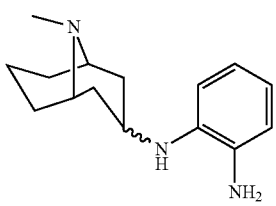
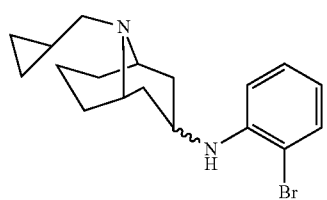 [SMILES: Brc1ccccc1NC1CC2CCCC(C1)N2CC1CC1]
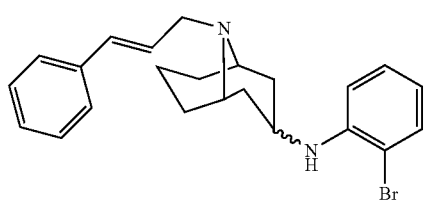 [SMILES: Brc1ccccc1NC1CC2CCCC(C1)N2C/C=C/c1ccccc1]
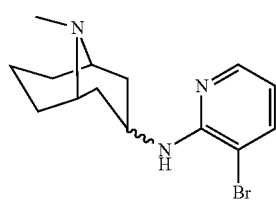 [SMILES: CN1C2CCCC1CC(Nc1ncccc1Br)C2]

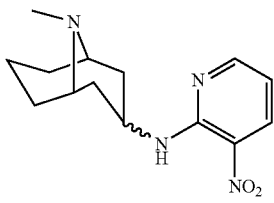
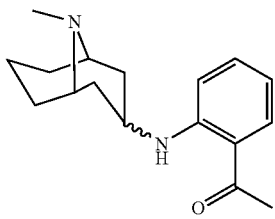 [SMILES: CC(=O)c1ccccc1NC1CC2CCCC(C1)N2C]
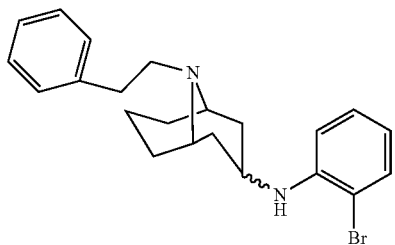 [SMILES: Brc1ccccc1NC1CC2CCCC(C1)N2CCc1ccccc1]
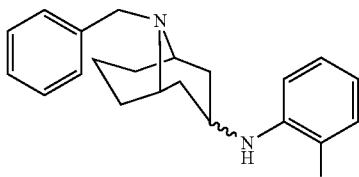
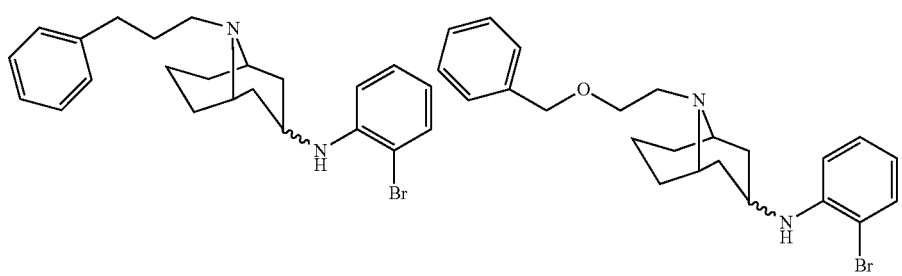
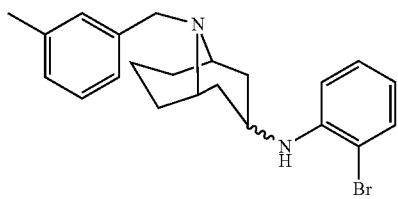 [SMILES: Cc1cccc(CN2C3CCCC2CC(Nc2ccccc2Br)C3)c1]
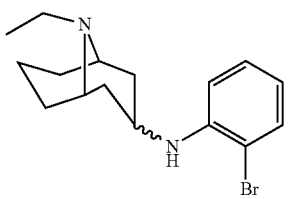 [SMILES: CCN1C2CCCC1CC(Nc1ccccc1Br)C2]
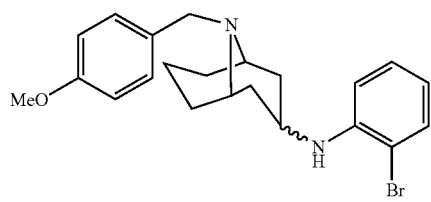 [SMILES: COc1ccc(CN2C3CCCC2CC(Nc2ccccc2Br)C3)cc1]
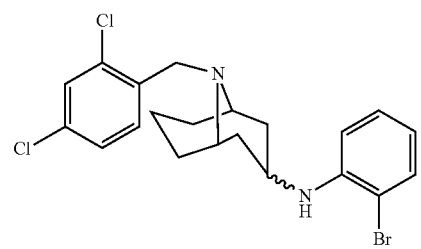 [SMILES: Clc1ccc(CN2C3CCCC2CC(Nc2ccccc2Br)C3)c(Cl)c1]
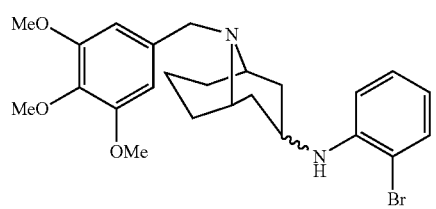 [SMILES: COc1cc(CN2C3CCCC2CC(Nc2ccccc2Br)C3)cc(OC)c1OC]
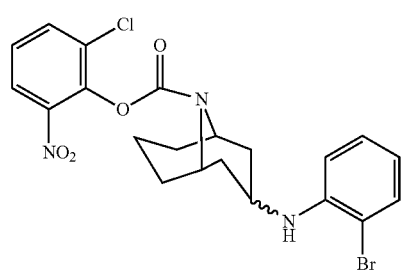 [SMILES: O=C(Oc1c([N+](=O)[O-])cccc1[N+](=O)[O-])N1C2CCCC1CC(Nc1ccccc1Br)C2]

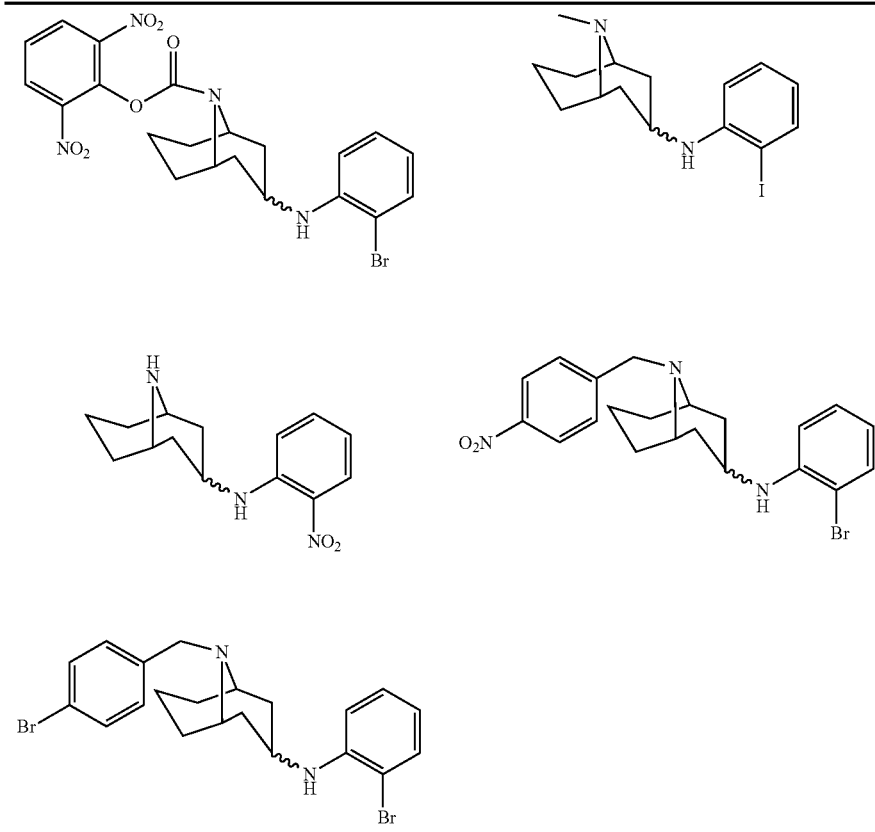

In some embodiments, the compounds disclosed herein have less than about 10 μM affinity for the α3β4 nicotinic acetylcholine receptor. In other embodiments, the compounds disclosed herein have less than about 2 μM affinity for the α3β4 nicotinic acetylcholine receptor. In other embodiments, the compounds disclosed herein have less than about 0.5 μM affinity for the α3β4 nicotinic acetylcholine receptor.

In some embodiments, the alpha isomer of the compounds disclosed herein have less than about 10 μM affinity for the α3β4 nicotinic acetylcholine receptor. In some embodiments, the alpha isomer of the compounds disclosed herein have less than about 2 μM affinity for the α3β4 nicotinic acetylcholine receptor. In other embodiments, the alpha isomer of the compounds disclosed herein have less than about 0.5 μM affinity for the α3β4 nicotinic acetylcholine receptor.

In some embodiments, the alpha isomer of the compounds disclosed herein has greater affinity for the α3β4 nicotinic acetylcholine receptor than the beta isomer of the compounds disclosed herein.

Preparation of the Compounds

In general, the compounds of Formula (I) may be prepared by methods well known to those of skill in the art in organic chemistry. As illustrated in Scheme 1, Compound A, which may be made by known synthetic methods may be treated with an amino compound to provide the intermediate imino compound B which upon reduction yield desired compound C.

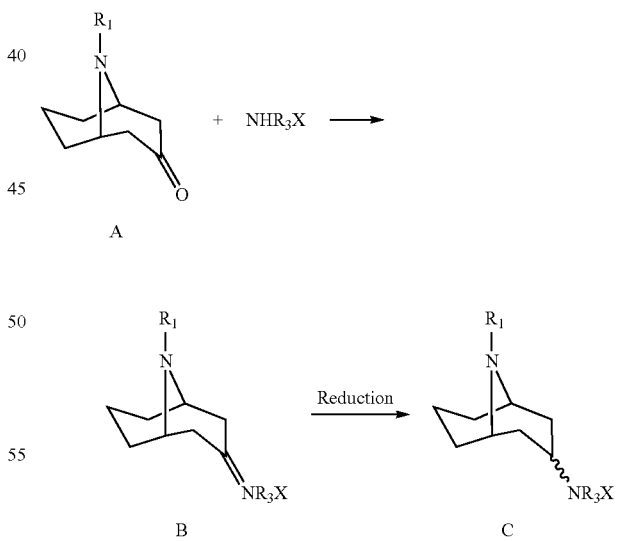

Scheme 1

Alternatively, as illustrated in Scheme 2, in situ reduction of the intermediate hydroxylamine adduct provides the amine B' which may be cross coupled using transition metal chemistry, for example, with a phenyl halide to provide compound C'. Those of skill in the art will appreciate that that the amine B' may also be cross coupled with aryl and heteroaryl halides.

Scheme 2

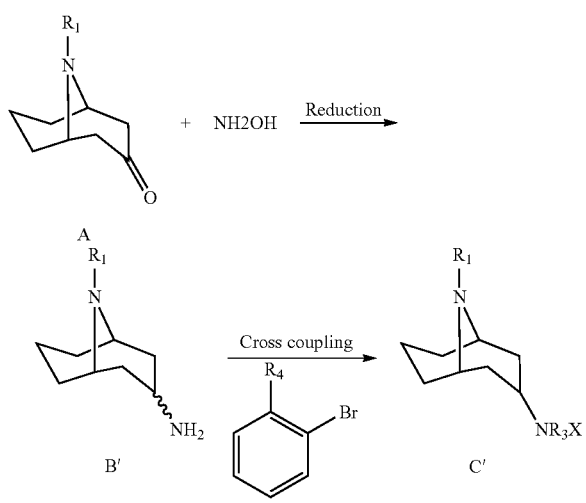

Pharmaceutical Compositions and Methods of Administration

The pharmaceutical compositions provided herein contain therapeutically effective amounts of one or more of the compounds provided herein that are useful in the prevention, treatment, or amelioration of one or more of the symptoms of diseases or disorders described herein and a pharmaceutically acceptable vehicle. Pharmaceutical vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in some embodiments, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as topical administration, transdermal administration and inhaled administration via nebulizers, pressurized metered dose inhalers and dry powder inhalers. In some embodiments, the compounds described above are formulated into pharmaceutical compositions using techniques and procedures well known in the art (see, e.g., Ansel Introduction to Pharmaceutical Dosage Forms, Seventh Edition (1999).

In the compositions, effective concentrations of one or more compounds or pharmaceutically acceptable derivatives thereof is (are) mixed with a suitable pharmaceutical vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the pharmaceutically acceptable vehicle in an amount sufficient to exert a therapeutically useful effect in the absence of undesirable side effects on the patient treated. The therapeutically effective concentration may be determined empirically by testing the compounds in in vitro and in vivo systems well known to those of skill in the art and then extrapolated therefrom for dosages for humans. Human doses are then typically fine-tuned in clinical trials and titrated to response.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In some embodiments, a therapeutically effective dosage should produce a serum concentration of active ingredient of from about 0.001 ng/ml to about 50-200 µg/ml. The pharmaceutical compositions, in other embodiments, should provide a dosage of from about 0.0001 mg to about 70 mg of compound per kilogram of body weight per day. Pharmaceutical dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN®, or dissolution by enhanced ionization (i.e., dissolving in aqueous sodium bicarbonate). Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined The pharmaceutical compositions are provided for administration to humans and animals in unit dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

In certain embodiments, the compositions are lactose-free compositions containing excipients that are well known in the art and are listed, for example, in the *U.S. Pharmacopeia* (USP) 25-NF20 (2002). In general, lactose-free compositions contains active ingredients, a binder/filler, and a lubricant in pharmaceutically compatible and pharmaceutically acceptable amounts. Particular lactose-free dosage forms contain active ingredients, microcrystalline cellulose, pre-gelatinized starch, and magnesium stearate.

Further provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene laural ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or pharmaceutically acceptable derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. patent Nos. RE28,819 and 4,358,603. Briefly, such formulations include, but are not limited to, those containing a compound provided herein, a dialkylated mono- or poly-alkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (Tween® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of pharmaceutically active compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321: 574 (1989). In other embodiments, polymeric materials can be used. In other embodiments, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984). In some embodiments, a controlled release device is introduced into a subject in proximity of the site of inappropriate immune activation or a tumor. Other controlled release systems are discussed in the review by Langer (*Science* 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbital, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044, 126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

For nasal administration, the preparation may contain an esterified phosphonate compound dissolved or suspended in a liquid carrier, in particular, an aqueous carrier, for aerosol application. The carrier may contain solubilizing agents such as propylene glycol, surfactants, absorption enhancers such as lecithin or cyclodextrin, or preservatives.

These solutions, particularly those intended for ophthalmic use, may be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point.

Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same pharmaceutically acceptable substance and by the same methods as for formulations for oral administration.

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or pharmaceutically acceptable derivatives may be packaged as articles of manufacture containing packaging material, a compound or pharmaceutically acceptable derivative thereof provided herein, which is effective for treatment, prevention or amelioration of one or more symptoms of the diseases or disorders, supra, within the packaging material, and a label that indicates that the compound or composition, or pharmaceutically acceptable derivative thereof, is used for the treatment, prevention or amelioration of one or more symptoms of the diseases or disorders, supra.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

Dosages

In human therapeutics, the physician will determine the dosage regimen that is most appropriate according to a preventive or curative treatment and according to the age, weight, stage of the disease and other factors specific to the subject to be treated. The pharmaceutical compositions, in other embodiments, should provide a dosage of from about 0.0001 mg to about 70 mg of compound per kilogram of body weight per day. Pharmaceutical dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form. The amount of active ingredient in the formulations provided herein, which will be effective in the prevention or treatment of a disorder or one or more symptoms thereof, will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject.

Exemplary doses of a formulation include milligram or microgram amounts of the active compound per kilogram of subject or sample weight (e.g., from about 1 micrograms per kilogram to about 50 milligrams per kilogram, from about 10 micrograms per kilogram to about 30 milligrams per kilogram, from about 100 micrograms per kilogram to about 10 milligrams per kilogram, or from about 100 microgram per kilogram to about 5 milligrams per kilogram).

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

Methods of Use of the Compounds and Compositions

Methods of treating, preventing, or ameliorating medical disorders such as, for example, drug addiction (e.g., cocaine addiction, opiate addiction (e.g., heroin, morphine, oxycontin tramdol, etc.), amphetamine (e.g., methamphetamine, dexedrine, MDMA, etc.), nicotine addiction, alcohol addiction marijuana addiction or combinations and modifications thereof), pain, neurodegenerative disorders, Parkinson's disease, Alzheimer's disease, and psychiatric disorders (e.g., schizophrenia) are also provided herein. In practicing the methods, effective amounts of the compounds or compositions containing therapeutically effective concentrations of the compounds are administered.

In some embodiments, methods for modulating a nicotinic acetylcholine receptor (nAChR) are provided herein. In other embodiments, methods of antagonizing receptors such as, for example, the α3β4 nicotinic acetylcholine receptor are also provided herein. In still other embodiments, the compounds of Formula (I) are more than 200 times more selective for the α3β4 nicotinic acetylcholine receptor than the α4β2 nicotinic acetylcholine receptor. In still other embodiments, the compounds of Formula (I) are more than 100 times more selective for the α3β4 nicotinic acetylcholine receptor than the α4β2 nicotinic acetylcholine receptor. In still other embodiments, the compounds of Formula (I) are more than 50 times more selective for the α3β4 nicotinic acetylcholine receptor than the α4β2 nicotinic acetylcholine receptor. In still other embodiments, the compounds of Formula (I) are more than 10 times more selective for the α3β4 nicotinic acetylcholine receptor than the α4β2 nicotinic acetylcholine receptor. In practicing the methods, therapeutically effective amounts of the compounds or compositions, described herein, supra, are administered.

Combination Therapy

The compounds and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration of one or more symptoms associated with drug addiction, pain, neurodegenerative disorders, Parkinson's disease, Alzheimer's disease, and psychiatric disorders (e.g., schizophrenia).

It should be understood that any suitable combination of the compounds and compositions provided herein with one or more of the above therapeutic agents and optionally one or more further pharmacologically active substances are considered to be within the scope of the present disclosure. In some embodiments, the compounds and compositions provided herein are administered prior to or subsequent to the one or more additional active ingredients.

It should also be understood that any suitable combination of the compounds and compositions provided herein may be used with other agents to antagonize the α3β4 nicotinic acetylcholine receptor.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

The following examples are provided for illustrative purposes only and are not intended to limit the scope of the invention.

EXAMPLES

General: $^1$H NMR spectra were recorded on a Varian Gemini 300 MHz spectrometer (300 MHz and 75 MHz, respectively) and are internally referenced to chloroform at δ 7.27. Data for $^1$H NMR are reported as follows: chemical shift (δ ppm), multiplicity (s=singlet, d=doublet, t=triplet, q=quartet, m=multiplet), coupling constant (Hz), integration, and assignment. Mass spectra were obtained using a ThermoFinnigan LCQ Duo LC/MS/MS instrument and an electrospray ionization probe. Thin-layer chromoatgraphy was run on Analtech Uniplate silica gel TLC plates. Flash chromatography was carried out using silica gel, Merck grade 9385, 230-400 mesh.

Example 1

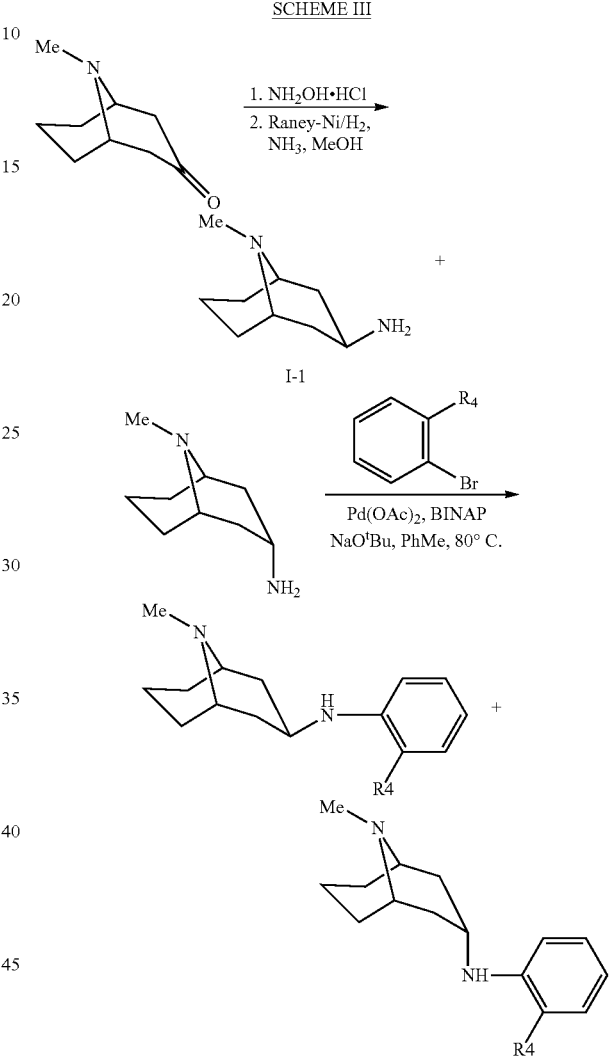

SCHEME III

General Method:
Step 1: 9-methyl-9-azabicyclo[3.3.1]nonan-3-amine (Compound I-1).

To a 250 mL RB flask were added 9-methyl-9-azabicyclo [3.3.1]nonan-3-one (10 g), NH$_2$OH.HCl (5.26 g), NaOAc.3H$_2$O (10.26 g), EtOH (56 mL), and H$_2$O (26 mL). The mixture was refluxed for 1.5 h and cooled to RT. Solvents were removed and the residue was partitioned between aqueous K$_2$CO$_3$ (3M) and CHCl$_3$. The organic phase was separated and the aqueous phase extracted twice with CHCl$_3$. The combined CHCl$_3$ solution was washed once with brine, dried over Na$_2$SO$_4$, filtered, and evaporated to a brownish oil, which solidified upon standing. The solid was transferred to a 500 mL Parr flask. To this were added Raney-Ni (6.2 g, wet) and NH$_3$ solution in MeOH (150 mL), made by bubbling NH$_3$ into MeOH for 20 min. This mixture was hydrogenated under a pressure of 40-45 psi of H$_2$ at RT for 18 h. The mixture was filtered through a pad of Celite. All volatiles were removed on a rotary evaporator. EtOH (50 mL) was added to the residue and then evaporated to give an I-1 as an oil (9.5 g, 94%). This crude product contained two isomers, and was used without further purification.

Step 2: Coupling with Substituted Aryl Bromide.

The amine I-1, obtained from step 1 (1 eq), 2-substituted bromobenzene (2 eq), Pd(OAc)$_2$ (2 mol %), rac-BINAP (2 mol %), NaO$^t$Bu (4 eq) and PhMe (3 mL/mmol) were mixed in a Schlenk flask, and stirred at 80° C. till the reaction was complete (2-3 h). The resulting deep-colored mixture was partitioned between ethyl acetate and water. The organic phase was separated and the aqueous phase extracted once with ethyl acetate. The combined ethyl acetate solution was washed with brine, dried over Na$_2$SO$_4$, filtered, and evaporated to a deep-colored oil, which was subjected to chromatography on silica gel, eluting with DCM/MeOH (containing 10% NH$_3$.H$_2$O) (95/5 to 90/10). Two isomers were usually obtained. Data for the less polar isomer is reported below.

N-(2-bromophenyl)-9-methyl-9-azabicyclo[3.3.1]nonan-3-amine: free base was obtained in 51% yield as a foamy solid. R$_f$ 0.31. $^1$H NMR (300 MHz, CDCl$_3$) δ ppm 7.40 (dd, J=7.8, 1.5 Hz, 1H), 7.15 (ddd, J=8.4, 6.9, 1.2 Hz, 1H), 6.77 (dd, J=8.1, 0.9 Hz, 1H), 6.51 (ddd, J=7.8, 7.5, 1.2 Hz, 1H), 4.07 (d, J=8.1 Hz, 1H), 4.04-3.84 (m, 1H), 3.08 (d, J=10.8 Hz, 2H), 2.64-2.56 (m, 2H), 2.51 (s, 3H), 2.06-1.91 (m, 3H), 1.59-1.47 (m, 1H), 1.24 (ddd, J=12.3, 7.8, 2.7 Hz, 2H), 1.06-0.94 (m, 2H); MS (ESI) m/z 309, 311 (M+H)$^+$. Free base was treated with HCl/Et$_2$O solution to give the HCl salt as an off-white powder.

N-(2-chlorophenyl)-9-methyl-9-azabicyclo[3.3.1]nonan-3-amine: free base was obtained in 55% yield as a foamy solid. $^1$H NMR (400 MHz, CDCl$_3$) δ ppm 7.23 (dd, J=8.0, 1.6 Hz, 1H), 7.11 (ddd, J=7.8, 7.0, 1.6 Hz, 1H), 6.80 (dd, J=8.2, 1.0 Hz, 1H), 6.57 (ddd, J=7.6, 7.6, 1.2 Hz, 1H), 4.04 (d, J=8.4 Hz, 1H), 4.15-3.86 (m, 1H), 3.09 (d, J=10.8 Hz, 2H), 2.56 (td, J=12.0, 6.0 Hz, 2H), 2.51 (s, 3H), 2.08-1.94 (m, 3H), 1.60-1.45 (m, 1H), 1.24 (ddd, J=12.4, 9.2, 3.2 Hz, 2H), 1.06-0.94 (m, 2H); MS (ESI) m/z 265 (M+H)$^+$. Free base was treated with HCl/Et$_2$O solution to give the HCl salt as an off-white powder.

N-(2-trifluoromethylphenyl)-9-methyl-9-azabicyclo[3.3.1]nonan-3-amine: free base was obtained in 41% yield as a foamy solid. $^1$H NMR (400 MHz, CDCl$_3$) δ ppm 7.32-7.26 (m, 2H), 6.76 (d, J=9.2 Hz, 1H), 6.55 (ddd, J=7.6, 7.6, 0.8 Hz, 1H), 4.21 (d, J=8.4 Hz, 1H), 4.01 (br, 1H), 3.07 (d, J=10.4 Hz, 2H), 2.54-2.42 (m, 2H), 2.45 (s, 3H), 2.00-1.85 (m, 3H), 1.55-1.45 (m, 1H), 1.22 (ddd, J=12.4, 10.8, 3.2 Hz, 2H), 1.04-0.92 (m, 2H); MS (ESI) m/z 256 (M+H)$^+$. Free base was treated with HCl/Et$_2$O solution to give the HCl salt as an off-white powder.

N-(2-nitrophenyl)-9-methyl-9-azabicyclo[3.3.1]nonan-3-amine: free base was obtained in 54% yield as an orange waxy solid. $^1$H NMR (400 MHz, CDCl$_3$) δ ppm 8.14 (dd, J=8.8, 1.6 Hz, 1H), 7.99 (d, J=7.2 Hz), 7.41 (ddd, J=7.8, 7.8, 0.8 Hz, 1H), 7.06 (d, J=8.8 Hz, 1H), 6.60 (ddd, J=7.8, 7.2, 1.2 Hz, 1H), 4.22 (s, 1H), 3.22 (d, J=10.0 Hz, 2H), 2.70-2.50 (m, 2H), 2.58 (s, 3H), 2.10-1.91 (m, 3H), 1.65-1.50 (m, 1H), 1.41 (ddd, J=12.5, 11.0, 3.0 Hz, 2H), 1.09 (s, br, 2H); MS (ESI) m/z 276 (M+H)$^+$. Free base was treated with HCl/Et$_2$O solution to give the HCl salt as orange crystals.

N-(2-cyanophenyl)-9-methyl-9-azabicyclo[3.3.1]nonan-3-amine: free base was obtained in 18% yield as a yellowish solid. $^1$H NMR (400 MHz, CDCl$_3$) δ ppm 7.32-7.26 (m, 2H), 6.78 (d, J=8.8 Hz, 1H), 6.55 (ddd, J=7.6, 7.6, 0.8 Hz, 1H), 4.20 (d, J=8.4 Hz, 1H), 4.04 (s, br, 1H), 3.08 (d, J=11.4 Hz, 2H), 2.55-2.43 (m, 2H), 2.47 (s, 3H), 2.10-1.84 (m, 3H), 1.58-1.44 (m, 1H), 1.23 (ddd, J=12.6, 11.0, 3.2 Hz, 2H), 1.05-0.94 (m, 2H); MS (ESI) m/z 256 (M+H)$^+$.

(2-((9-methyl-9-azabicyclo[3.3.1]nonan-3-yl)amino)phenyl)(phenyl)methanone: free base was obtained in 28% yield as a yellow solid. $^1$H NMR (400 MHz, CDCl$_3$) δ ppm 8.62 (d, J=7.6 Hz, 1H), 7.62-7.57 (m, 2H), 7.53-7.41 (m, 4H), 6.92 (d, J=8.4 Hz, 1H), 6.47 (ddd, J=7.5, 7.0, 1.0 Hz, 1H), 4.14-4.01 (m, 1H), 3.11 (d, J=11.2 Hz, 2H), 2.65-2.54 (m, 2H), 2.52 (s, 3H), 2.12-1.94 (m, 3H), 1.58-1.48 (m, 1H), 1.38 (ddd, J=12.4, 10.8, 3.2 Hz, 2H), 1.08-0.97 (m, 2H); MS (ESI) m/z 335 (M+H)$^+$.

N-(2-iodophenyl)-9-methyl-9-azabicyclo[3.3.1]nonan-3-amine: free base was obtained in 53% yield as a waxy solid. $^1$H NMR (400 MHz, CDCl$_3$) δ ppm 7.40 (dd, J=7.8, 1.4 Hz, 1H), 7.17 (ddd, J=7.8, 7.0, 1.4 Hz, 1H), 6.70 (dd, J=8.0, 1.2 Hz, 1H), 6.39 (ddd, J=7.4, 7.2, 1.6 Hz, 1H), 4.00-3.84 (m, 2H), 3.08 (d, J=11.2 Hz, 2H), 2.62-2.49 (m, 2H), 2.50 (s, 3H), 2.08-1.92 (m, 3H), 1.59-1.49 (m, 1H), 1.30-1.20 (m, 2H), 1.05-0.95 (m, 2H); MS (ESI) m/z 357 (M+H)$^+$. Free base was treated with HCl/Et$_2$O solution to give HCl salt as a white powder.

Example 2

SCHEME IV

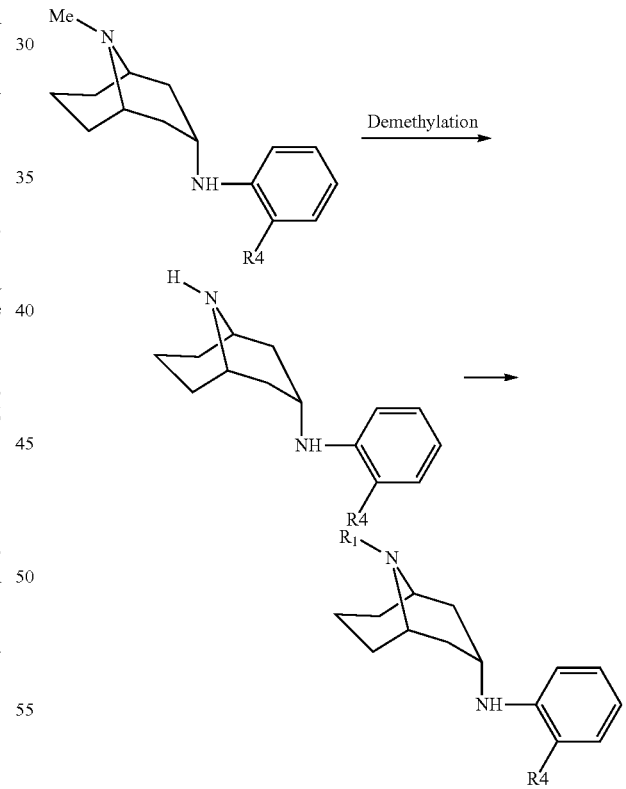

General Method:

Demethylation: To a mixture of N-(2-R$_4$-phenyl)-9-methyl-9-azabicyclo[3.3.1]nonan-3-amine (1 eq) and NaHCO$_3$ (10 eq) in DCE (15 mL/mmol), at 0° C., was added 1-chloroethyl chloroformate (10-15 eq). The resulting mixture was refluxed overnight. After cooling to RT, the reaction mixture was poured to Na$_2$CO$_3$ (2N) and extracted with DCM (2×). The combined extract was washed with brine, dried over MgSO$_4$, filtered and evaporated dryness. The residue was dissolved in EtOH (10 mL/mmol) and refluxed for 3 h. All volatiles were removed to give crude product. This crude material can be used without further purification for reductive amination. Pure product was obtained by chromatography on silica gel, eluting with DCM/MeOH (10% NH$_3$.H$_2$O) (95/5 to 80/20).

N-(2-bromophenyl)-9-azabicyclo[3.3.1]nonan-3-amine: free base was obtained in 92% yield as a waxy solid. $^1$H NMR (400 MHz, CDCl$_3$) δ ppm 7.40 (dd, J=8.0, 1.6 Hz, 1H), 7.15 (ddd, J=7.7, 7.0, 1.4 Hz, 1H), 6.74 (dd, J=8.4, 1.6 Hz, 1H), 6.53 (ddd, J=7.5, 7.4, 1.4 Hz, 1H), 4.07 (d, J=8.0 Hz, 1H), 3.73-3.60 (m, 1H), 3.44-3.35 (m, 2H), 2.50-2.36 (m, 2H), 1.98 (qt, J=13.2, 4.6, 1H), 1.65 (tt, J=13.0, 4.4, 2H), 1.60-1.50 (m, 1H), 1.48-1.39 (m, 2H), 1.16 (ddd, J=12.7, 12.0, 3.6 Hz, 2H); MS (ESI) m/z 295, 297 (M+H)$^+$.

N-(2-nitrophenyl)-9-azabicyclo[3.3.1]nonan-3-amine: free base was obtained in 91% yield as an orange solid. $^1$H NMR (400 MHz, CDCl$_3$) δ ppm 8.16 (dd, J=8.6, 1.4 Hz, 1H), 7.98 (d, br, J=7.2 Hz, 1H), 7.41 (ddd, J=7.8, 7.2, 1.2 Hz, 1H), 6.97 (d, J=8.4, 1.6 Hz, 1H), 6.60 (ddd, J=8.5, 7.0, 1.4 Hz, 1H), 3.97-3.83 (m, 1H), 3.49-3.38 (m, 2H), 2.53-2.40 (m, 2H), 2.06-1.90 (m, 1H), 1.72-1.53 (m, 3H), 1.52-1.42 (m, 2H), 1.30 (ddd, J=12.8, 12.0, 3.6 Hz, 2H); MS (ESI) m/z 262 (M+H)$^+$.

Reductive amination: To a mixture of N-(2-R$_4$-phenyl)-9-azabicyclo[3.3.1]nonan-3-amine hydrochloride (1 eq) and the appropriate aldehyde (1.5-2.0 eq) in 1,2-dichloroethane was successively added NaBH(OAc)$_3$ (2.0-3.0 eq), and HOAc (1.0-2.0 eq). The resulting suspension was stirred at RT till the starting amine disappeared. The mixture was partitioned between ethyl acetate and NaHCO$_3$ (sat.). The organic phase was separated and the aqueous one extracted once with ethyl acetate. The combined ethyl acetate solution was washed with brine, dried over Na$_2$SO$_4$, filtered, and evaporated to oil, which was subjected to chromatography on silica gel, eluting with ethyl acetate/hexane (0/100 to 30/70).

N-(2-bromophenyl)-9-cinnamyl-9-azabicyclo[3.3.1]nonan-3-amine: free base was obtained in 81% yield as a yellowish waxy solid. $^1$H NMR (400 MHz, DMSO-d$_6$) δ ppm 7.44-7.38 (m, 3H), 7.36-7.29 (m, 2H), 7.23 (tt, J=7.4, 1.6 Hz, 1H), 7.18 (ddd, J=7.6, 7.2, 1.6 Hz, 1H), 6.78 (dd, J=8.2, 1.4 Hz, 1H), 6.56 (d, J=16.0 Hz, 1H), 6.53 (ddd, J=7.6, 7.2, 1.6 Hz, 1H), 6.24 (dt, J=16.0, 6.4 Hz, 1H), 4.20-3.90 (m, 1H), 3.49 (dd, J=6.4, 1.6 Hz, 2H), 3.22 (d, J=11.2 Hz, 2H), 2.54 (ddd, J=12.0, 12.0, 5.6 Hz, 2H), 2.14-2.00 (m, 1H), 1.94 (tt, J=13.2, 4.4 Hz, 2H), 1.55 (d, J=12.8 Hz, 1H), 1.32-1.22 (m, 2H), 1.18-1.10 (m, 2H); MS (ESI) m/z 411, 413 (M+H)$^+$. Free base was treated with HCl/Et$_2$O solution to give HCl salt as an off-white solid.

N-(2-bromophenyl)-9-(3-phenylpropyl)-9-azabicyclo[3.3.1]nonan-3-amine: free base was obtained in 65% yield as a colorless oil. $^1$H NMR (400 MHz, CDCl$_3$) δ ppm 7.41 (dd, J=7.8, 1.4 Hz, 1H), 7.36-7.14 (m, 6H), 6.69 (d, J=8.4 Hz, 1H), 6.53 (ddd, J=7.6, 6.8, 1.6 Hz, 1H), 4.06 (d, J=8.4 Hz, 1H), 3.90-3.76 (m, 1H), 3.18 (d, J=11.2 Hz, 2H), 2.90 (t, J=7.6 Hz, 2H), 2.73 (t, J=7.6 Hz, 2H), 2.48 (td, J=7.8, 6.0 Hz, 2H), 2.00 (qt, J=13.4, 4.0 Hz, 1H), 1.89 (tt, J=13.2, 4.0 Hz, 2H), 1.52 (d, J=13.6 Hz, 1H), 1.23 (ddd, J=12.8, 11.0, 2.8 Hz, 2H), 1.03 (d, J=12.4 Hz, 2H); MS (ESI) m/z 399, 401 (M+H)$^+$. Free base was treated with HCl/Et$_2$O solution to give HCl salt as a white solid.

N-(2-bromophenyl)-9-(4-methoxybenzyl)-9-azabicyclo[3.3.1]nonan-3-amine: free base was obtained in 11% yield as oil. $^1$H NMR (400 MHz, CDCl$_3$) δ ppm 7.33 (d, J=8.0 Hz, 1H), 7.21 (d, J=8.4 Hz, 2H), 7.11 (t, J=7.6 Hz, 1H), 6.80 (d, J=8.4 Hz, 2H), 6.68 (d, J=8.0 Hz, 1H), 6.44 (t, J=7.4 Hz, 1H), 4.08-3.84 (m, 2H), 3.74 (s, 3H), 3.72 (s, 2H), 3.05 (d, J=10.8 Hz, 2H), 2.48 (td, J=12.0, 5.6 Hz, 2H), 2.08-1.83 (m, 3H), 1.49 (d, J=12.4 Hz, 1H), 1.26-1.10 (m, 2H), 0.94 (d, J=12.0 Hz, 2H); MS (ESI) m/z 415, 417 (M+H)$^+$. Free base was treated with HCl/Et$_2$O solution to give HCl salt as an off-white solid.

N-(2-bromophenyl)-9-(4-bromobenzyl)-9-azabicyclo[3.3.1]nonan-3-amine: free base was obtained in 61% yield as an orange solid. $^1$H NMR (400 MHz, CDCl$_3$) δ ppm 8.17 (d, J=8.8 Hz, 1H), 8.02 (d, J=7.6 Hz, 1H), 7.45 (d, J=8.4 Hz, 2H), 7.44 (t, J=7.2 Hz, 1H), 7.45 (d, J=8.4 Hz, 2H), 6.95 (d, J=8.4 Hz, 1H), 6.61 (t, J=7.6 Hz, 1H), 4.22-4.08 (m, 1H), 3.80 (s, 2H), 3.12 (d, J=10.8 Hz, 2H), 2.51 (td, J=12.0, 6.0 Hz, 2H), 2.12-1.90 (m, 3H), 1.59 (d, J=10.0 Hz, 1H), 1.39 (ddd, J=12.6, 11.2, 1.2 Hz, 2H), 1.06 (d, J=11.6 Hz, 2H); MS (ESI) m/z 430, 432 (M+H)$^+$. Free base was treated with HCl/Et$_2$O solution to give HCl salt as an orange solid.

Example 3

In vitro Testing of Ligands at α3β4 and α4β2 receptors for binding affinity in competition with [$^3$H]epibatidine The Ki±SEM was determined for each compound in competition with [$^3$H]epibatidine. Compounds are tested on membranes derived from HEK cells that have been transfected with rat α3β4 and α4β2 receptors. Specific experiments are described below:

Cell Culture. KX α3β4R2 and KX α4β2R2 cells are cultured in Dulbecco's modified Eagle's medium (DMEM), supplemented with 10% fetal bovine serum (FBS), 0.5% penicillin/streptomycin, and 0.4 mg/ml of geneticin. The cells are maintained in an atmosphere of 7.5% CO$_2$ in a humidified incubator at 37° C. For binding assays, cells are plated on 100-mm dishes. For functional assays, the cells are seeded into 96-well collagen-coated plates (Becton Dickinson Biocoat) at a density of approximately 50,000 cells/well. Cells seeded at this density grow into a confluent monolayer in 24 to 30 h.

Binding Assays. Cells are harvested by scraping the plates with a rubber policeman and then centrifuged at 500×g (2200 rpm) for 10 min. The cell pellet is suspended in Tris buffer, homogenized in a Polytron Homogenizer, and centrifugation repeated twice at 20,000×g (13,500 rpm) for 20 min. Cells are finally suspended in 5 ml of Tris buffer to determine their protein content. For binding, the cell membrane is incubated with the test compounds at concentrations ranging from 10$^{-5}$ to 10$^{-10}$ M in the presence of 0.3 nM of [$^3$H]epibatidine. After 3 h of incubation at room temperature, samples are filtered through glass fiber filters and presoaked in 0.1% polyethyleneimine (PEI) by using a Tomtec cell harvester. Filters are counted on a betaplate reader (Wallac). Nonspecific binding is determined by using 0.1 μM of the unlabeled epibatidine. Full characterization of compounds includes analysis of the data for IC$_{50}$ values and Hill coefficients by using the program PRISM. Ki values will be calculated using the Cheng Prusoff transformation:

$$Ki = \frac{IC50}{1 + L/Kd}$$

Where, L is radioligand concentration and Kd is the binding affinity of the radioligand, as determined previously by saturation analysis. Typically the compounds disclosed herein had greater than 2 uM affinity for the α3β4 nicotinic acetylcholine receptor with selectivity of at least 10× for the α3β4 nicotinic acetylcholine receptor when compared with the α4β2 nicotinic acetylcholine receptor.

What is claimed is:

1. A compound of Formula (I):

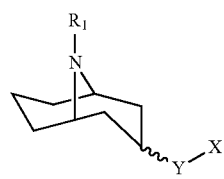

or salts, hydrates or solvates thereof wherein:
- $R_1$ is hydrogen, alkyl, substituted alkyl, heteroalkyl, substituted heteroalkyl, arylalkyl, substituted arylalkyl, heteroarylalkyl, substituted heteroarylalkyl or —$CO_2R_2$;
- $R_2$ is alkyl, substituted alkyl, heteroalkyl, substituted heteroalkyl, aryl, substituted aryl, arylalkyl, substituted arylalkyl, heteroaryl, substituted heteroaryl, heteroarylalkyl or substituted heteroarylalkyl;
- Y is —$NR_3$;
- $R_3$ is hydrogen, alkyl, substituted alkyl, arylalkyl, substituted arylalkyl heteroarylalkyl or substituted heteroarylalkyl;
- X is o-substituted phenyl.

2. The compound of claim 1, wherein $R_1$ is hydrogen, alkyl, substituted alkyl, arylalkyl, substituted arylalkyl or —$CO_2R_2$.

3. The compound of claim 1, wherein $R_1$ is hydrogen, alkyl or substituted alkyl.

4. The compound of claim 1, wherein $R_1$ is hydrogen, methyl, ethyl,

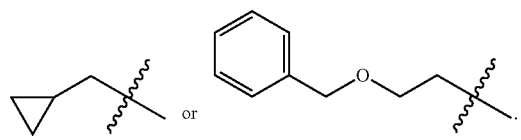 [SMILES: *CC1CC1 ; *CCOCc1ccccc1]

5. The compound of claim 1, wherein $R_1$ is arylalkyl or substituted arylalkyl.

6. The compound of claim 1, wherein $R_1$ is

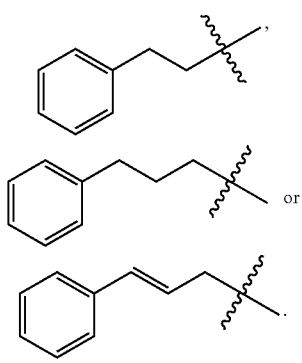

7. The compound of claim 1, wherein $R_1$ is

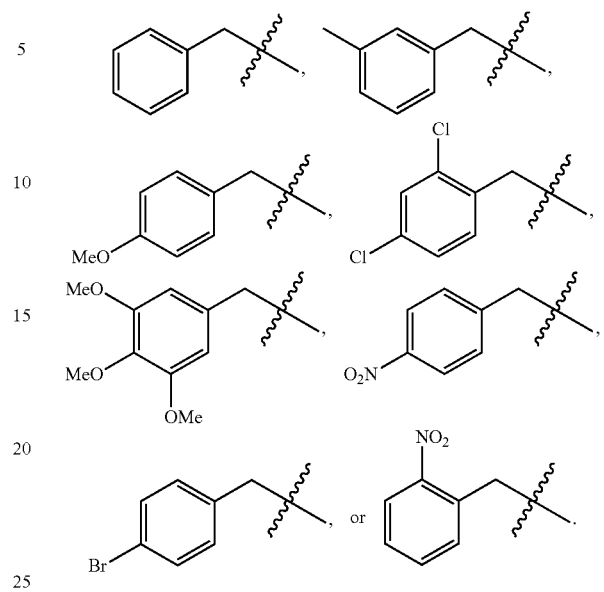

8. The compound of claim 1, wherein $R_1$ is —$CO_2R_2$ and $R_2$ is disubstituted phenyl.

9. The compound of claim 1, wherein $R_2$ is

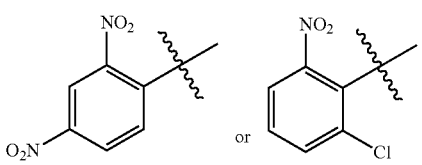

10. The compound of claim 1, wherein X is

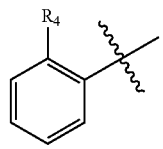

and $R_4$ is —Cl, —Br, —F, —I, —$CH_3$—$CF_3$, —$OCF_3$, —OH, —$CO_2t$—Bu, —$NO_2$, —$NH_2$, —$COCH_3$ or —CN.

11. The compound of claim 1, wherein $R_3$ is hydrogen, or $C_{1-6}$ alkyl.

12. The compound of claim 1, wherein Y is —NH— or —$NCH_3$—.

13. The compound of claim 1, wherein $R_1$ is hydrogen, alkyl, substituted alkyl, arylalkyl, substituted arylalkyl or —$CO_2R_2$, and Y is —NH— or —$NCH_3$—.

14. The compound of claim 1, wherein $R_1$ is hydrogen, alkyl or substituted alkyl, and Y is —NH— or —$NCH_3$—.

15. The compound of claim 1, wherein $R_1$ is arylalkyl or substituted arylalkyl and Y is —NH— or —$NCH_3$—.

16. The compound of claim 1, wherein $R_1$ is —$CO_2R_2$, $R_2$ is disubstituted phenyl and Y is —NH— or —$NCH_3$—.

17. The compound of claim 1, wherein $R_1$ is hydrogen, methyl, ethyl,

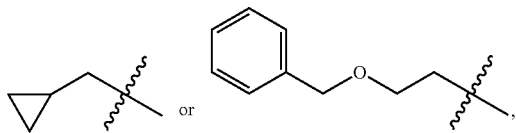 [SMILES: *CC1CC1 ; *CCOCc1ccccc1] or , and Y is —NH— or —NCH$_3$—.

18. The compound of claim 1, wherein R$_1$ is

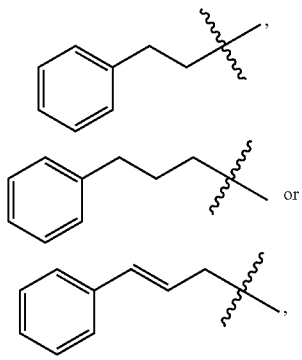

and Y is —NH— or —NCH$_3$—.

19. The compound of claim 1, wherein R$_1$ is

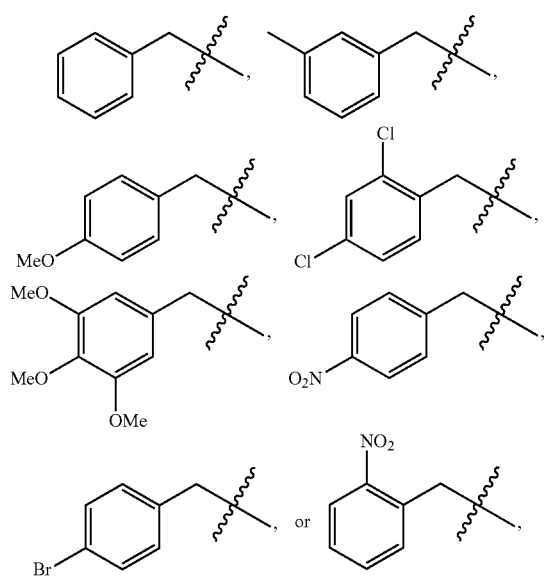

and Y is —NH— or —NCH$_3$—.

20. The compound of claim 1, wherein R$_1$ is —CO$_2$R$_2$, R$_2$ is

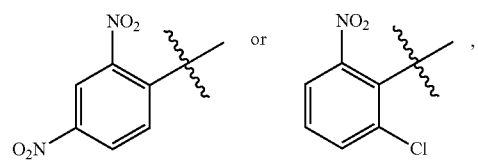 [SMILES: *c1ccc([N+](=O)[O-])cc1[N+](=O)[O-] ; *c1c(Cl)cccc1[N+](=O)[O-]]

and Y is —NH— or —NCH$_3$—.

21. The compound of claim 1, wherein R$_1$ is hydrogen, alkyl, substituted alkyl, arylalkyl, substituted arylalkyl or —CO$_2$R$_2$, X is

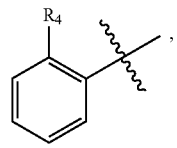

R$_4$ is —Cl, —Br, —F, —I, —CH$_3$ —CF$_3$, —OCF$_3$, —OH, —CO$_2$t—Bu, —NO$_2$, —NH$_2$, —COCH$_3$ or —CN and Y is —NH— or —NCH$_3$—.

22. The compound of claim 1, wherein R$_1$ is hydrogen, alkyl or substituted alkyl, X is

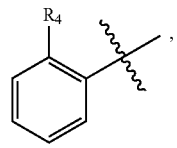

R$_4$ is —Cl, —Br, —F, —I, —CH$_3$ —CF$_3$, —OCF$_3$, —OH, —CO$_2$t—Bu, —NO$_2$, —NH$_2$, —COCH$_3$ or —CN and Y is —NH— or —NCH$_3$—.

23. The compound of claim 1, wherein R$_1$ is arylalkyl or substituted arylalkyl, X is

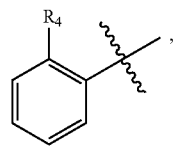

R$_4$ is —Cl, —Br, —F, —I, —CH$_3$ —CF$_3$, —OCF$_3$, —OH, —CO$_2$t—Bu, —NO$_2$, —NH$_2$, —COCH$_3$ or —CN and Y is —NH— or —NCH$_3$—.

24. The compound of claim 1, wherein R$_1$ is —CO$_2$R$_2$, R$_2$ is disubstituted phenyl, X is

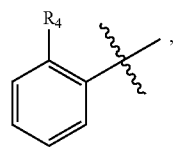

R$_4$ is —Cl, —Br, —F, —I, —CH$_3$ —CF$_3$, —OCF$_3$, —OH, —CO$_2$t—Bu, —NO$_2$, —NH$_2$, —COCH$_3$ or —CN and Y is —NH— or —NCH$_3$—.

25. The compound of claim 1, wherein R$_1$ is hydrogen, methyl, ethyl,

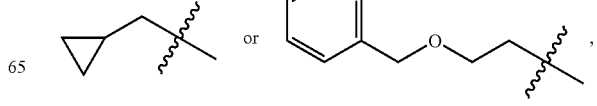

-continued

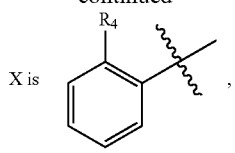

R₄ is —Cl, —Br, —F, —I, —CH₃ —CF₃, —OCF₃, —OH, —CO₂t—Bu, —NO₂, —NH₂, —COCH₃ or —CN and Y is —NH— or —NCH₃—.

26. The compound of claim 1, wherein R₁ is

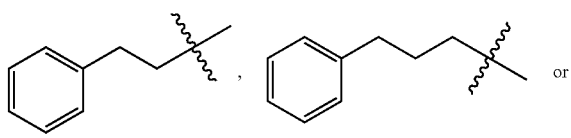

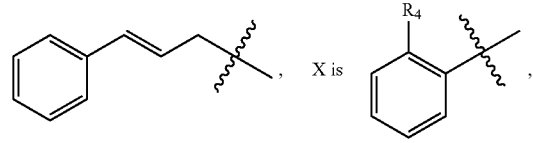

R₄ is —Cl, —Br, —F, —I, —CH₃ —CF₃, —OCF₃, —OH, —CO₂t—Bu, —NO₂, —NH₂, —COCH₃ or —CN and Y is —NH— or —NCH₃—.

27. The compound of claim 1, wherein R₁ is

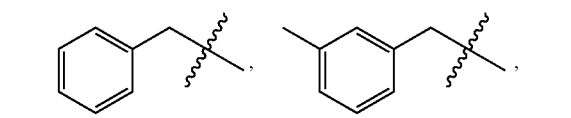

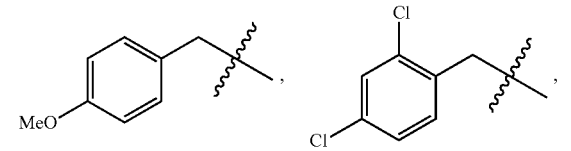

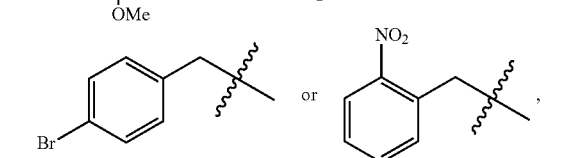

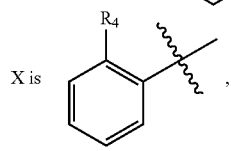

R₄ is —Cl, —Br, —F, —I, —CH₃ —CF₃, —OCF₃, —OH, —CO₂t—Bu, —NO₂, —NH₂, —COCH₃ or —CN and Y is —NH— or —NCH₃—.

28. The compound of claim 1, wherein R₁ is —CO₂R₂, R₂ is

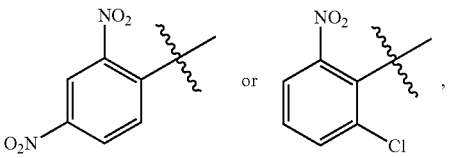

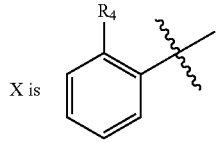

R₄ is —Cl, —Br, —F, —I, —CH₃ —CF₃, —OCF₃, —OH, —CO₂t—Bu, —NO₂, —NH₂, —COCH₃ or —CN and Y is —NH— or —NCH₃—.

29. The compound of claim 1, wherein R₁ is methyl, Y is —NH and X is

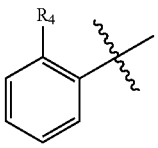

and R₄ is —Cl, —Br, —F, —I, —CH₃ —CF₃, —OCF₃, —OH, —CO₂t—Bu, —NO₂, —NH₂, —COCH₃ or —CN.

30. The compound of claim 1, wherein R₁ is methyl, Y is —NH— and X is

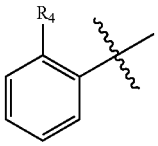

and R₄ is —Cl, —Br, —F, —I, —CF₃, —OCF₃, —NO₂ or —CN.

31. The compound of claim 1, wherein R₁ is methyl, Y is —NCH₃— and X is

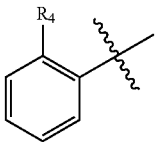

and R₄ is —Br.

32. The compound of claim 1, wherein R₁ is hydrogen, Y is —NH— and X is

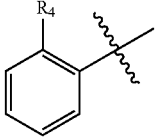

and R₄ is —NO₂.

33. The compound of claim 1, wherein $R_1$ is ethyl,

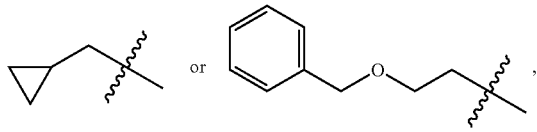 [SMILES: *CC1CC1 ; *CCOCc1ccccc1]

Y is —NH— and X is

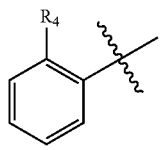

and $R_4$ is —Br.

34. The compound of claim 1, wherein $R_1$ is hydrogen, Y is —NH— and X is

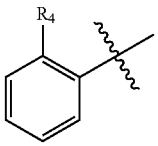

and $R_4$ is —Br.

35. A pharmaceutical composition comprising the compound of claim 1 and a pharmaceutically acceptable vehicle.

36. A pharmaceutical composition comprising the compound of claim 25 and a pharmaceutically acceptable vehicle.

37. A pharmaceutical composition comprising the compound of claim 34 and a pharmaceutically acceptable vehicle.

38. A pharmaceutical composition comprising the compound of claim 27 and a pharmaceutically acceptable vehicle.

39. A pharmaceutical composition comprising the compound of claim 30 and a pharmaceutically acceptable vehicle.

* * * * *

UNITED STATES PATENT AND TRADEMARK OFFICE
CERTIFICATE OF CORRECTION

PATENT NO.        : 9,062,042 B2          Page 1 of 1
APPLICATION NO.   : 13/004801
DATED             : June 23, 2015
INVENTOR(S)       : Zaveri et al.

It is certified that error appears in the above-identified patent and that said Letters Patent is hereby corrected as shown below:

In the Specification

In column 1, line 9, delete "DA20811" and insert -- 1 R01 DA020811 --, therefor.

In column 1, line 10, delete "on Drug Abuse" and insert -- of Health (NIH) --, therefor.

Signed and Sealed this
Twenty-sixth Day of April, 2016

Michelle K. Lee
*Director of the United States Patent and Trademark Office*